United States Patent
Kremenchugsky et al.

[11] Patent Number: 5,803,915
[45] Date of Patent: Sep. 8, 1998

[54] SYSTEM FOR DETECTION OF PROBE DISLODGEMENT

[75] Inventors: Vladimir Kremenchugsky, Reisterstown; Steven M. Falk, Silver Spring; Jeffrey A. Taylor, Columbia; Charles M. Moskowitz, Owings Mills; Steven L. Hardesty, Pasadena, all of Md.

[73] Assignee: Ohmeda Inc., Liberty Corner, N.J.

[21] Appl. No.: 568,912

[22] Filed: Dec. 7, 1995

[51] Int. Cl.$^6$ .............................. A61B 5/00; G01K 17/00
[52] U.S. Cl. ............................... 600/549; 374/29
[58] Field of Search ..................... 128/736, 713, 128/738, 633–634; 374/29–30; 600/549

[56] References Cited

U.S. PATENT DOCUMENTS

| | | | |
|---|---|---|---|
| 4,294,263 | 10/1981 | Hochman | 128/736 |
| 4,399,823 | 8/1983 | Donnelly | 128/736 |
| 4,399,824 | 8/1983 | Davidson | 128/735 |
| 4,541,728 | 9/1985 | Hauser et al. | 374/29 |
| 4,859,078 | 8/1989 | Bowman et al. | 128/736 X |
| 4,865,044 | 9/1989 | Wallace et al. | 128/736 |
| 5,109,849 | 5/1992 | Goodman et al. | 128/698 X |

FOREIGN PATENT DOCUMENTS

| | | |
|---|---|---|
| 0 059 701 | 9/1982 | European Pat. Off. . |
| 2 059 053 | 4/1981 | United Kingdom . |
| 2 061 496 | 5/1981 | United Kingdom . |
| WO 83/01189 | 4/1983 | WIPO . |

*Primary Examiner*—Francis Jaworski
*Attorney, Agent, or Firm*—Roger M. Rathbun; Salvatore P. Pace

[57] ABSTRACT

A heat flux sensor is used in conjunction with a patient sensor, such as a patient temperature sensor, and which is secured to the patient in close proximity to the patient sensor. The heat flux sensor monitors the heat flux between the patient and the environment. Upon dislodgement of the patient probe, the heat flux sensor senses a change in heat flux that is of a predetermined amount and provides a signal indicating that the patient probe has become partially or fully dislodged from the patient. In the case of a patient heat sensor, the use of a heat flux sensor provides a quicker and larger signal than would be seen by merely monitoring the change in temperature due to partial or full probe dislodgement.

14 Claims, 2 Drawing Sheets

SYSTEM FOR DETECTION OF PROBE DISLODGEMENT

BACKGROUND OF THE INVENTION

This invention relates to probes for attachment to a patient to monitor the temperature or other physiological condition of the patient and to a system of accurately and quickly determining when that probe has become dislodged from the patient.

In particular, one type of probe to which this invention is specifically applicable and for which the description hereof will be applied, is an infant temperature probe that is conventionally affixed to the skin of an infant and which monitors the temperature of that infant's skin.

Such temperature probes are commonly used in the hospital nursery to control the application of heat to the infant, more specifically, various infant care centers or incubators include a heater, or plurality of heaters, that provide needed heat to the infant and the control of that heat is regulated by a skin temperature sensor affixed to the infant. Thus, if the skin temperature of the infant is lowered, the servo-control of such apparatus applies additional heat to that infant. Similarly, as the skin temperature of the infant exceeds the desired temperature, the temperature probe affixed to the infant senses that excess temperature and the servo-control of the heating apparatus reduces the power to the heater to reduce the heating to the infant.

A problem with the use of such infant skin temperature probes in controlling the heat applied to the infant, however, is that on occasion, the probe becomes dislodged from the infant. The problem is not uncommon since the infant may be somewhat active and the probe cannot be attached with strong adhesive or the like since there is the possibility of damage to the infant's skin upon normal removal of the temperature probe.

Accordingly, when the skin temperature probe is inadvertently dislodged, that sensor is no longer be receiving a signal indicative of the skin temperature of the infant. In many cases, a lower temperature will be sensed by the dislodged skin temperature probe since the probe may then merely be laying on the bottom of the infant warming apparatus. The servo-control thus increases the power to the heater in the mistaken interpretation that the infant's skin has been reduced and therefore believes that the infant needs additional heat.

As such, the heater can continue to increase in the heat intensity and cause difficulties to the infant. Other scenarios are, of course possible, since the dislodged probe can be sensing the temperature of any other item within the infant warming apparatus but in any case, the certainty is that the infant skin temperature sensor is providing an erroneous signal to the servo-control. Thus, the unit will not be properly be measuring the infant's skin temperature and applying the proper amount of heat to that infant.

Another problem associated with the dislodgement is in the case of a partial dislodgement where the temperature sensor may stay affixed to the infant but is not providing sufficient contact with the infants skin to properly sense that skin temperature. Again, the sensor will be providing erroneous skin temperature information to the servo-control such that, again, the proper quantity of heat is not being applied to the infant but further, in such case, the dislodgement may not be noticed by the attending personnel.

Various means have been attempted to detect the dislodgement of a skin temperature probe, such as disclosed in U.S. Pat. Nos. 4,399,823 and 4,399,824 and in the specifications of those patents. In the '823 and 824 patents, the skin temperature probe is a thermistor that is periodically heated and a control signal developed that is characteristic of the heat dissipation of the heated probe. That heat dissipation is, of course, different depending on whether the probe is secured to the infant or whether the probe has become dislodged.

One difficulty with that system is, however, that the periodic pulsing of the thermistor with heat invariably ages the thermistor and eventually causes a premature failure of the thermistor, that is, the frequent heating and cooling of a thermistor is not good for the device and ultimately affects its reliability. In addition, during the time period that the heating pulse is being applied to the probe, the probe must be taken out of its normal duty cycle of providing infant skin temperature information to the servo-control. Therefore, there is a certain downtime during which the probe is not carrying out its intended purpose of monitoring the infant's skin temperature in using the pulse method. If, of course, the infant needs heat during that period or periods, the servo-control will not be able to respond.

SUMMARY OF THE INVENTION

The present invention provides a novel probe for the detection of infant skin temperature that combines a means of sensing quickly and accurately, the dislodgement of the temperature probe from the skin of an infant. The probe includes the normal temperature sensor means contacting the infants skin, such as a thermistor, along with a heat flux sensor mounted in close proximity to the skin temperature sensor and sensing heat flux.

The heat flux sensor is used to directly measure the heat flux between the infant and the ambient and any dislodgement of the probe, or partial dislodgement, results in a relatively large magnitude in the change of heat flux between the patient and the ambient. Thus the change in signal from dislodgement or partial dislodgement is readily measurable and a system is also disclosed to detect that change in heat flux between the infant so as to trigger an alarm or take other corrective action to notify the attending personnel that the temperature sensor has become dislodged from the infant.

It should be noted that the present heat flux sensor may be used with a variety of sensors that are affixed to the skin and require integrity of that contact with the skin to provide good data. It is particularly useful in the case of temperature sensors, however, since many other sensors will immediately lose a signal and thus the fact that it has become dislodged is readily apparent. Such devices as EKG sensors are thus easy to verify contact or non-contact with the patient's skin since the monitor will immediately lose signal and an appropriate alarm can be triggered. With a temperature sensor, however, the temperature of the skin and the ambient may not be that different and thus the use of temperature difference to detect probe dislodgement can be slow if that is the only parameter used to detect the dislodgement.

Accordingly, in the preferred embodiment, a probe is provided that contains both a conventional or other skin temperature sensor as well as an additional sensor that measures the heat flux between the infants skin and the ambient. Again, as indicated, the preferred embodiment is set forth as a skin temperature probe for control of heat to an infant, however, it will readily be seen that the heat flux sensor can be used with other probes that attach to the skin of a patient.

In a further embodiment of the present invention, the heat flux sensor may be supplied as a separate sensor and be attached to or affixed to a conventional temperature sensor, such as a thermistor, to provide the advantages set forth herein of rapidly and accurately determining when the temperature sensor has become dislodged from the patient.

Other features of the novel probe and system for detecting probe dislodgement will become more apparent in light of the following detailed description of a preferred embodiment thereof and as illustrated in the accompanying drawings.

DETAILED DESCRIPTION OF PREFERRED EMBODIMENT

Figure 1:
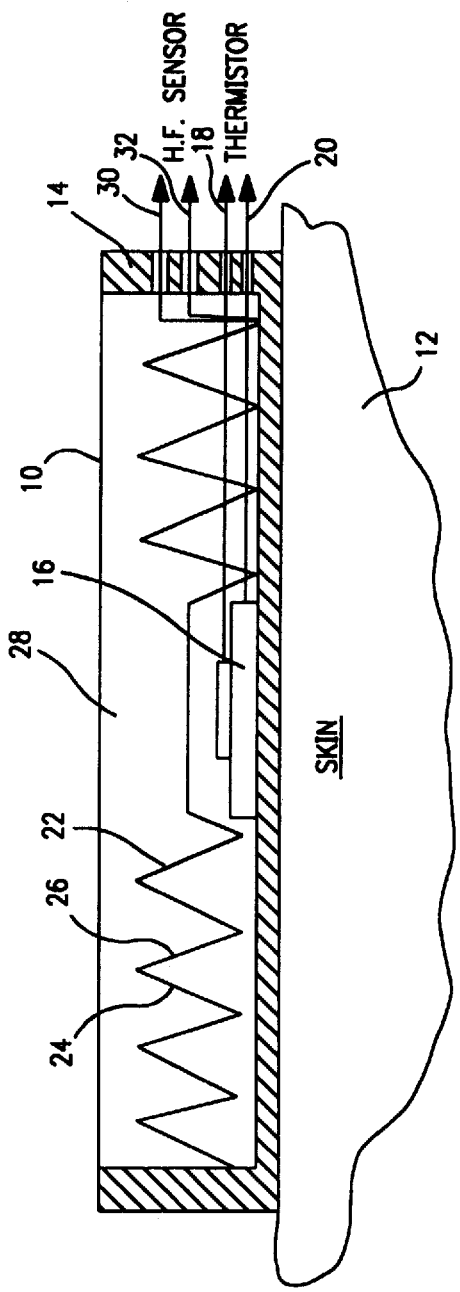
FIG. 1 is a schematic view of a patient probe constructed in accordance with the present invention.

Turning first to FIG. 1, there is shown a schematic view of a probe 10 constructed in accordance with the present invention. As described herein, the probe 10 will be described in terms of the preferred embodiment, that is, the probe 10 is a skin temperature probe used for the detection of the skin temperature of an infant within an infant warmer or other apparatus that provides heat to the infant. It is understood, however, that the present invention can be readily used to detect the dislodgement of any probe that is affixed to the skin of a patient to monitor some physical function or condition of the patient.

As shown, therefore, the probe 10 is affixed to the skin 12 of an infant and may be affixed thereto by conventional means such adhesive tape or the like. Probe 10 includes a housing 14 of good conductive material such as a thin metal or plastic composition. Contained within the housing is a temperature sensor 16 of conventional design and may be a thermistor to sense the skin temperature of the infant's skin 12. Such thermistors are currently supplied with infant warmers and are conventionally used to sense the skin temperature of the infant and provide a signal to a heater controller to control the amount of heat provided by that heater to the infant.

The signal from the temperature sensor 16 is transmitted to the various control circuitry of the infant warmer by means of wires 18, 20 as will later be explained.

Also contained within the housing 14 is a heat flux sensor 22 to detect the heat flux of heat that is transmitted from the infant or, in the case of some probes, to detect the heat flux of heat to the patient. The heat flux sensor is a commercially available item, one type of which is a thin film, asymptotic sensor available from Thermotics Co. of San Diego, Calif. Other suitable heat flux sensors may be of the type available from Hy Cal Engineering of El Monte, Calif.

As shown in the preferred embodiment, the heat flux sensor 22 comprises a spirally wound battery of thermoelectric elements, such as, for example alternating elements of copper 24 and constantan 26 that may entirely surround the temperature sensor 16 that is positioned at or near the center of the housing 14.

The heat flux sensor 22 may be encapsulated in a compound 28 having high thermal conductivity such as an epoxy. Again, a pair of electrical wires 30, 32 conduct the signal from the heat flux sensor 22 to external circuitry to be later explained.

Figure 2:
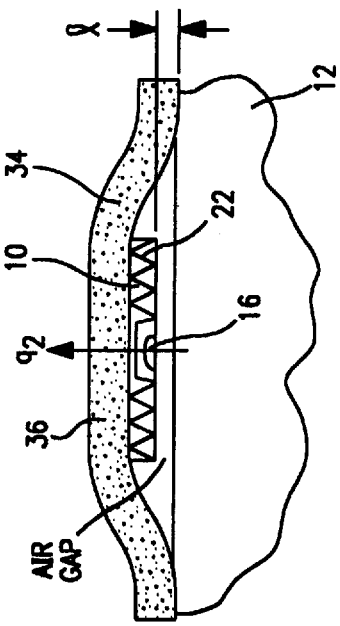
FIG. 2 is a an enlarged schematic view of a probe of FIG. 1 contacting the skin of a patient.
Figure 3:
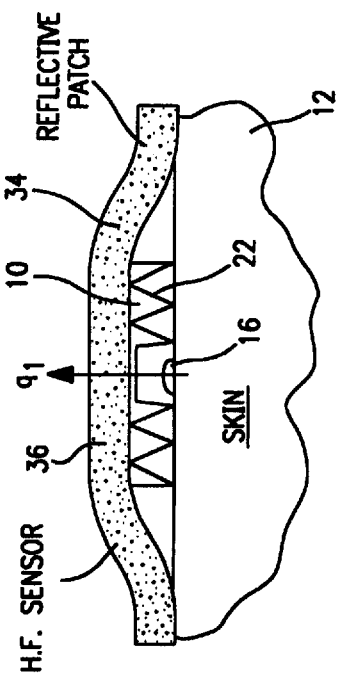
FIG. 3 is a further enlarged schematic view of the probe of FIG. 1 showing the probe in the dislodged position from the patient.

Turning now to FIGS. 2 and 3, there are shown schematic views of the probe 10 of the present invention both affixed to and dislodged from, respectively, the skin 12 of the infant. Taking the FIG. 2 schematic, the probe 10 is shown as being firmly affixed to the skin 12 of the infant. In FIG. 2, there is also shown, a reflective patch 34 that may be used to hold the probe 10 in position firmly affixed to the skin 12 of the infant and which may also have a layer 36 of a reflective material to reflect from the heat flux sensor and to insure that the proper value of heat flux between the infant and the ambient is measured. Generally, in the case of an infant within an infant heating apparatus, such as an infant incubator, the heat flux is in a direction from the infant to the ambient, however, it should be noted that the present invention may be applicable where the heat flux is in a direction toward the patient.

With the probe 10 firmly affixed to the patients skin 12, the temperature sensor 16 is properly monitoring the skin temperature of the infant and, as explained, the signals from the temperature sensor may be controlling the amount of heat provided to that infant. The heat flux density $q_1$ through the probe 10 is represented by the following equation:

$$q_1 = (T_S - T_A)/R_S$$

where $T_S$ is the skin temperature of the infant; $T_A$ is the ambient temperature and $R_S$ is the thermal resistance of the heat flux sensor. $R_S$ may be further defined by the equation:

$$R_S = \delta/k_S$$

where $\delta$ is the thickness of the heat flux sensor and $k_S$ is the thermal conductivity of the heat flux sensor.

Taking the condition of FIG. 3, where the probe 10 has become dislodged, the heat flux density for that condition is thus:

$$q_2 = (T_S - T_A)/(R_S + R_{AIR})$$

where $R_{AIR}$ is the thermal resistance of the air gap /.

There is an assumption that with small gap enclosures, there is only conductive heat exchange (F. Incopera and D. De Witt, Fundamentals of Heat and Mass Transfer, 3rd Edition, (1950), published by John Wiley and Sons, page 559.

Therefore, the rate of heat flux change due to the probe 10 becoming dislodged between the conditions of FIG. 2 and FIG. 3 can be described by the following equation:

$$(q_1 - q_2)/q_2 = 1 + R_{AIR}/R_S.$$

Taking some practical examples, using the value for the thermal conductivity of air from the F. Incopera and D. De Witt reference, infra, appendix ABBE as $k_{AIR}$ 0.0263 W/mK; the thermal conductivity of heat flux sensor filled with an epoxy based compound of approximately 0.3 W/mK and a sensor thickness of 2.0 mm.; and assuming the probe dislodgement 1 to be about 0.5 mm. we have:

$$(q_1 - q_2) = 1 + 2.9 \approx 4.0$$

Therefore, for a dislodgement of 0.5 mm, the heat flux changes by a factor of 4 or by about 400%. Thus, the smallest dislodgement can readily be detected by the use of monitoring the heat flux as opposed to attempting to determine the change in temperature as detected by the skin temperature sensor.

As a contrast, since temperature sensors are used in infant warmers in an environment where only small gradients of temperature exist, assume the temperature gradient between the infant's skin and the external ambient to be about 0.5° C., after dislodgement, by 0.5 mm., the temperature on the surface of the probe changes no more than 0.3° C. In such case, the resistance of a typical thermistor does not change more that about 2–3%. As shown, however, the change in the heat flux from the infant to the ambient for the same probe dislodgement is about 400%.

Accordingly, by monitoring and utilizing the change in heat flux to detect small air gaps (dislodgements) the ability to detect such gaps is considerably higher than by the detection of a change in temperature of the skin temperature sensor.

Figure 4:
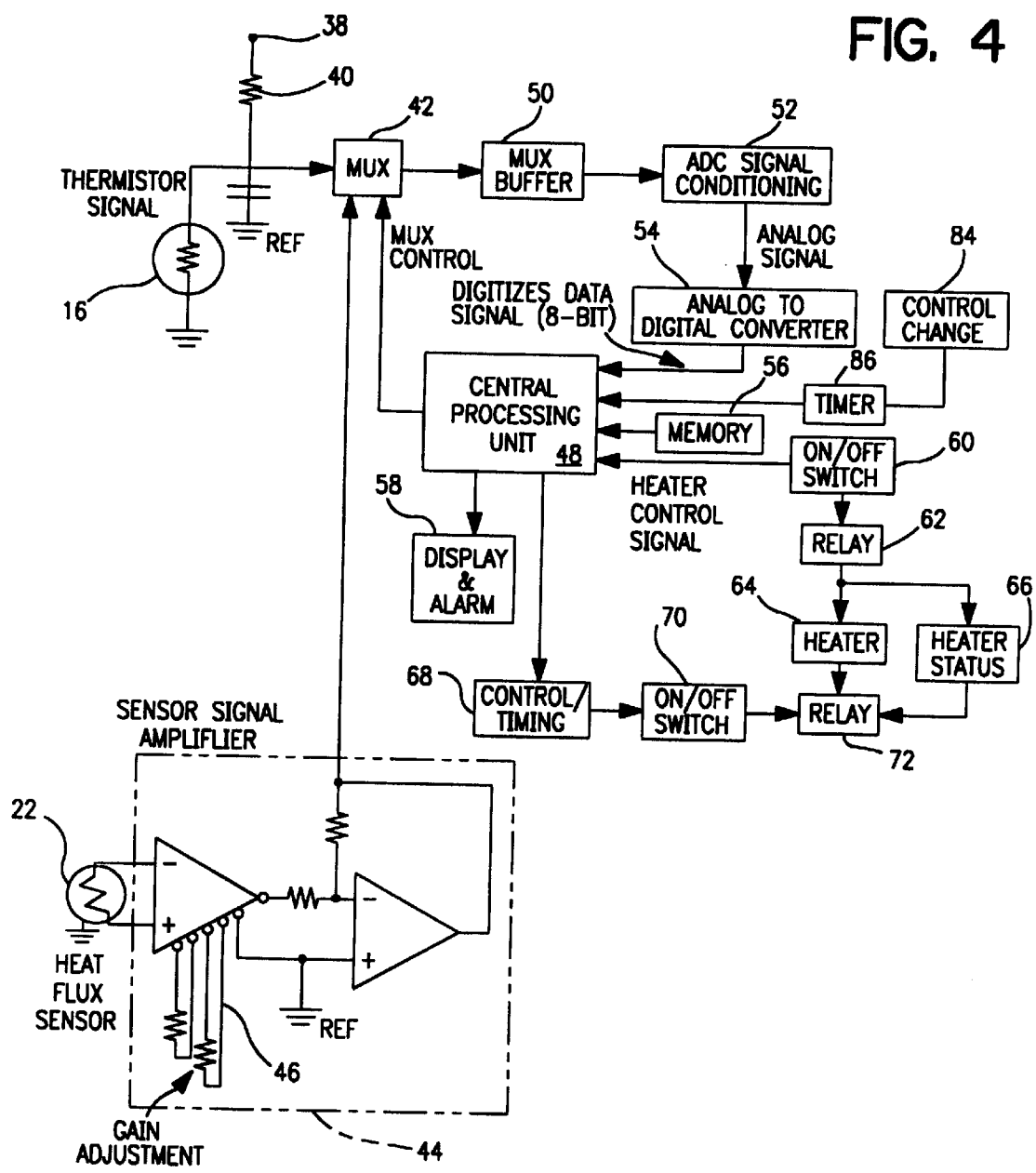
FIG. 4 is a block diagram of a control circuit usable for carrying out the present invention.

Turning now to FIG. 4, there is shown a block diagram of a circuit for receiving the signals from the temperature sensor 16 and the heat flux sensor 22 and which is used to determine when a dislodgement has taken place.

As stated, temperature sensor 16 is preferably a standard thermistor currently available and used on infant warmers to monitor the infant's skin temperature and control the application of heat by means of a conventional servo-controlled heater. Such thermistor may generally have a negative temperature coefficient whereby its electrical resistance varies inversely with the temperature of the skin of the infant, that is, as the skin temperature of the infant increases, the resistance of the thermistor decreases.

A reference voltage is supplied to the thermistor via a source 38 and current-limiting resistor 40. As is usual with such devices, when the thermistor is applied to the skin of the infant whereby the resistance of the thermistor changes for a period of time whereupon it reaches a steady state where its resistance is indicative of the skin temperature of the infant.

That signal, in the form of a analog voltage output is fed into multiplexer 42.

The heat flux sensor 22 comprises the plurality of thermocouples as previously described and also may include a signal amplifier 44 to increase the strength of the signal and a gain adjustment 46 such that signal strength can be adjusted as desired to match the characteristics of the later components. The heat flux sensor 22 actually generates a voltage indicative of the heat flux and therefore requires amplification and tuning to arrive a normalized value.

As shown, the signal from the heat flux sensor 22 and which is thus indicative of the heat flux from the infant, after amplification, is also fed into multiplexer 42. The multiplexer 42 thus receives the signals as voltage signals from the temperature sensor 16 and the heat flux sensor 22 and a central processing unit (CPU) 48 selects which signal is to be processed at any one time. The multiplexer 42 may switch back and forth between the input signals at the rate of about 1 megahertz.

After one of the signals from the temperature sensor 16 or heat flux sensor 22 is selected by the CPU 48, that signal is processed through the multiplexer buffer 50 where an impedance matching takes place so that the signal can be conditioned. That signal is thus conditioned in the ADC signal conditioning circuit 52 which provides reference voltages and other signal conditioning required to amplify the analog signal and filter out noise. That signal is converted from analog to digital form in analog to digital converter 54, and the digitized signal fed into the CPU 48.

The CPU 48 thus controls the intermittency of the signals from the temperature sensor 16 and heat flux sensor 22 and receives, in digital form, a data train signal representative of those signals. Once in digital form, the CPU 48 can easily monitor the signals from both sensors and determine changes in the signals. For example, by use of memory 56, a continuous tracking of the magnitude of signals from the heat flux sensor 22 can be maintained and the CPU 48 can determine and provide a signal whenever the signal from the heat flux sensor 22 changes by a predetermined amount, thus indicating that the overall probe 10 has become partially or fully dislodged from the skin of the infant.

That signal can be provided to a display and alarm 58 so that the operator can be advised of the dislodgement immediately and can take the corrective action.

The heater circuits are also shown in FIG. 4 and which are controlled by the CPU 48 acting on the signals from the temperature sensor 16. Such circuits are currently used and are conventional and include an on/off switch 60 controlled by the CPU 48 to activate a relay 62 controlling the heater 64. A redundant circuit may generally be used to make sure the heater 64 is operating with its intended cycle and includes a heater status circuit 66 that continuously monitors the status of the heater 64 so that the CPU 48 knows whether the heater 64 is in the on or off state. A control/timing circuit 68 communicates with the CPU 48 and checks on the operation of the heater operation by receiving information as to the heater status via off/on switch 70 that receives the data from a relay 72 operable from the heater status circuit 66.

Finally, a timing circuit is included to deactivate the processing of data by the CPU 48 under conditions that the control of the heater providing heat to the infant is changed. As an example, a control change circuit 84 detects when a change has been made in the heater for the infant and a timer 86 receives that signal and deactivates the CPU 48 from sending an alarm signal during a predetermined amount of time.

As, for example, the infant care unit is initially activated and the temperature sensor 16 secured to the skin of the infant, the heater providing heat to the infant is turned on to bring the infant up to the predetermined temperature. During the power up procedure, the change in heat flux to the infant is of a large magnitude and, unless deactivated, would send an erroneous alarm signal to the display and alarm 58 and the user would be bothered by a false alarm.

Similarly, when the operator of the infant care apparatus changes the set temperature desired for the infant, the heat flux again experiences a change of high magnitude as the infant care apparatus adjusts the infant to that temperature. At that point, the control change circuit 84 recognizes that the change in the temperature set point has been effected and temporarily deactivates the CPU 48 from sending an erroneous alarm signal.

Accordingly, with the circuit processing of FIG. 4, a constant monitoring of the level of heat flux between the infant and the ambient can be achieved and an alarm triggered or other corrective action taken if the heat flux changes by a predetermined amount indicative of the probe becoming partially or fully dislodged from the infant.

Figure 5:
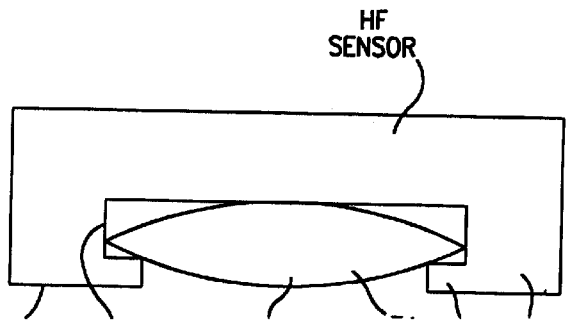
FIG. 5 is a schematic view of a further embodiment of the flux sensor constructed in accordance with the present invention used in proximity with a conventional temperature sensor.

Finally, turning to FIG. 5, there is shown a schematic view of a combination of a temperature sensor 74 and a heat flux sensor 76 that have been physically attached so as to carry out the purposes and achieve the advantages of the present invention.

In the FIG. 5 embodiment, the temperature sensor 74 is a standard thermistor and which is conventionally supplied with current infant warmers and its dimensions are known and are standard. Rather that completely change the temperature sensor of conventional infant warmers, the heat flux sensor 76 is manufactured to have the same heat flux sensor internally as in the FIG. 1 embodiment, however the heat flux sensor 74 is in the form of an annulus with a center opening 78 that is dimensioned so as to fit over the conventional thermistor. Various means may be used, such as a lip 80 to secure the heat flux sensor 76 to the temperature sensor 74 so that the two sensors are firmly affixed together with both functioning to be affixed to the infants skin as in the prior embodiment.

Preferably an adhesive 82 may be applied to the annular surface of the heat flux sensor 74 to enable the heat flux sensor 74 and the thermistor to be secured to the patient. Thus the heat flux sensor 74 not only provides an indication of probe dislodgement but also serves to affix the thermistor to the patient. In this combined unit, it is important that the thermistor and the heat flux sensor be maintained in close proximity to each other and preferable in direct contact to the extent possible. It is also important that the surface of the thermistor and the surface of the heat flux sensor that actually contacts the patient to preferably be coplanar.

Accordingly, the heat flux sensor 76 may carry out the purpose of detecting the dislodgement of the temperature sensor 74 but can be attached in the field to conventionally sized thermistors and, of course, the additional signal processing will also need to be added to the control circuity of conventional infant warmers. As noted, the means to attach the two sensors together may be with the lip 80 or the heat flux sensor 76 may be sized so as to by secured to the temperature sensor 74 by means such as an adhesive or epoxy cement in the particular field location. By any such means, the he at flux sensor 76 may be retrofitted to thermistors currently in the field or added to thermistors by a simple operation to those currently sold with or for an infant warming apparatus.

While the invention has been disclosed and described with respect to a single embodiment, it will become apparent that variations and modifications may be made therein, and it is therefore intended in the following claims to cover each variation and modification as falls with in the true spirit and scope of the invention.

We claim:

1. A system for detecting the dislodgement of a patient probe affixed to the skin of a patient, said system comprising a probe having a probe housing, a patient sensor for sensing a desired physical characteristic of the patient, said patient sensor contained within said probe housing and adapted to be affixed to the skin of the patient to monitor the desired characteristic and provide a signal representative of such characteristic, a heat flux sensor located within said probe housing and adapted to be in direct contact with the skin of the patient when said patient probe is affixed to the patient to detect the amount of heat flux between the patients skin and the surrounding ambient air and to produce a signal representative of such heat flux, and control circuit means receiving the signal from said heat flux sensor, said control circuit providing a signal indicative of a change in the signal of said heat flux sensor monitor when said heat flux sensor becomes dislodged from direct contact with the skin of the patient.

2. A system as defined in claim 1 wherein said patient sensor is a patient temperature sensor.

3. A system as defined in claim 2 wherein said patient sensor is a thermistor.

4. A system as defined in claim 1 wherein said heat flux sensor is a thin film asymptotic sensor.

5. A system as defined in claim 1 wherein said heat flux sensor is comprised of a spirally wound battery of copper and constantan elements.

6. A system as defined in claim 1 wherein said heat flow sensor and said patient sensor have coplanar surfaces adapted to both contact the skin of said patient when said patient probe is affixed to said patient.

7. A method of determining the dislodgement of a patient sensor affixed to the skin of a patient comprising:

affixing a heat flux sensor to directly contact the skin of the patient and in close proximity to the patient sensor;

monitoring the heat flux sensed by the heat flux sensor to determine the heat flux to or from the patient and the ambient air and providing a signal representative of that flux;

providing a signal when a predetermined change takes place in the signal from the heat flux sensor indicating that the patient sensor has been dislodged from the patients skin.

8. A method as defined in claim 7 wherein the patient sensor is a temperature sensor.

9. A method as defined in claim 8 further providing the step of activating an alarm upon the providing of the signal indicating that the patient sensor has been dislodged from the patients skin.

10. A method as defined in claim 9 further including the step of selectively deactivating the alarm for a predetermined time under predetermined conditions.

11. A patient probe adapted to be affixed to the skin of a patient, said probe comprising a probe housing of a high conductivity material, a patient sensor for sensing a desired physical characteristic of the patient, said patient sensor contained within said probe housing and adapted to be affixed to the skin of the patient to monitor the desired characteristic and provide a signal representative of such characteristic, a heat flux sensor located within said probe housing and adapted to be affixed to the skin of the patient in direct contact with the skin of the patient to detect the amount of heat flux between the patients skin and the surrounding ambient air and to produce a signal representative of such heat flux.

12. A patient probe as defined in claim 11 wherein said patient sensor is a skin temperature sensor.

13. A patient probe as defined in claim 12 wherein said patient sensor is a thermistor.

14. A patient probe as defined in claim 11 wherein the surface of said patient probe affixed to the patients skin is coated with an adhesive.

* * * * *